(12) United States Patent
Liaw

(10) Patent No.: US 6,849,444 B2
(45) Date of Patent: Feb. 1, 2005

(54) **STRAINS OF *RHIZOPUS ORYZAE* AND USES THEREOF**

(75) Inventor: Hungming J. Liaw, Champaign, IL (US)

(73) Assignee: Archer Daniels Midland Company, Decatur, IL (US)

( * ) Notice: Subject to any disclaimer, the term of this patent is extended or adjusted under 35 U.S.C. 154(b) by 167 days.

(21) Appl. No.: 10/127,679

(22) Filed: Apr. 23, 2002

(65) Prior Publication Data

US 2003/0003553 A1 Jan. 2, 2003

Related U.S. Application Data

(60) Provisional application No. 60/286,379, filed on Apr. 26, 2001.

(51) Int. Cl.$^7$ ................................................ C12N 1/14
(52) U.S. Cl. ............................ 435/256.6; 435/254.9; 435/139
(58) Field of Search .......................... 435/256.6, 254.9, 435/139

(56) References Cited

U.S. PATENT DOCUMENTS

| | | | | |
|---|---|---|---|---|
| 4,234,577 | A | 11/1980 | Zilliken | 424/238 |
| 4,963,486 | A | 10/1990 | Hang | 435/139 |
| 5,595,893 | A | 1/1997 | Pometto, III et al. | 435/136 |
| 5,786,185 | A | 7/1998 | Tsao et al. | 435/139 |
| 5,932,455 | A | 8/1999 | Viljava et al. | 435/139 |
| 6,004,776 | A | 12/1999 | Giuseppin et al. | 435/69.1 |

OTHER PUBLICATIONS

Skory, C.D., "Isolation and Expression of Lactate Dehydrogenase Genes from *Rhizopus oryzae*," *Appl. Environ. Microbiol.* 66:2343–2348, American Society for Microbiology (Jun. 2000).

Tay, A., and Yang, S.–T., "Production of L(+)–Lactic Acid From Glucose and Starch by Immobilized Cells of *Rhizopus oryzae* in a Rotating Fibrous Bed Bioreactor," *Biotechnol. Bioeng.* 80:1–12, Wiley Periodicals, Inc. (Oct. 2002).

Goldberg I., and Stieglitz, B., "Improved Rate of Fumaric Acid Production by Tweens® and Vegetable Oils in *Rhizopus arrhizus*," *Biotechnol. Bioeng.* 27:1067–1069, John Wiley & Sons, Inc. (1985).

Hang, Y.D., et al., "Production of L(+)–Lactic Acid by *Rhizopus oryzae* Immobilized in Calcium Alginate Gells," *Biotechnol. Lett.* 11:119–120, Kluwer Academic Publishers (1989).

Hang, Y.D., "Direct Fermentation of Corn to L(+)–Lactic Acid by *Rhizopus oryzae*," *Biotechnol. Lett.* 11:299–300, Kluwer Academic Publishers (1989).

Hang, Y.D., "Chitosan Production from *Rhizopus oryzae* Mycelia," *Biotechnol. Lett.*12:911–912, Kluwer Academic Publishers (1990).

Park, E.Y., et al., "Efficient Production of L–(+)–Lactic Acid Using Mycelial Cotton–like Flocs of *Rhizopus oryzae* in an Air–Lift Bioreactor," *Biotechnol. Prog.* 14:699–704, American Chemical Society and American Institute of Chemical Engineers (1998).

Pritchard, G.G., "Factors Affecting the Activity and Synthesis of NAD–dependent Lactate Dehydrognease in *Rhizopus oryzae*," *Gen. Microbiol.* 78:125–137, Cambridge University Press (1973).

Soccol, C.R., et al., "Production of L–lactic acid by Rhizopus species," *World. J. Microbiol. Biotechnol.* 10:433–435, Rapid Communications of Oxford Ltd. (1994).

Soccol, C.R., et al., "Potential of solid state fermentation for production of L(+)–lactic acid by *Rhizopus oryzae*," *Appl. Microbiol. Biotechnol.* 41:286–290, Springer–Verlag (1994).

Ward, G.E., et al., "Biochemical Studies in the Genus Rhizopus. I. The Production of Dextro–Lactic Acid" *J. Am. Chem. Soc.* 58:1286–1288, Mack Printing Co. (1936).

Yinhua, L., et al., "Extractive L–lactic Acid Fermentation with Immobilized *Rhizopus oryzae* in a Three–Phase Fluidized Bed," *Chin. J. Biotechnol.* 13:169–176, Allerton Press, Inc. (1997).

Yu, R.–c., and Hang, Y.D., "Kinetics of Direct Fermentation of Agricultural Commodities to L(+) Lactic Acid by *Rhizopus oryzae*," *Biotechnol. Lett.* 11:597–600, Kluwer Academic Publishers (1989).

Yu, R.–c., and Hang, Y.D., "Amylolytic enzyme production by *Rhizopus oryzae* grown on agricultural commodities," *World J. Microbiol. Biotechnol.* 6:15–18, Rapid Communications of Oxford Ltd. (1990).

Yu, R.–c., and Hang, Y.D., "Purification and Characterization of NAD–dependent Lactate Dehydrogenase from *Rhizopus oryzae*, " *Food Chem.* 41:219–225, Elsevier Science Publishers Ltd. (1991).

*Primary Examiner*—Irene Marx
(74) *Attorney, Agent, or Firm*—Kirkpatrick & Lockhart LLP

(57) ABSTRACT

Disclosed are novel strains of *Rhizopus oryzae* and uses thereof. The strains of the invention are temperature-resistant and convert a carbon source to lactic acid at high temperatures.

30 Claims, No Drawings

STRAINS OF *RHIZOPUS ORYZAE* AND USES THEREOF

CROSS-REFERENCE TO RELATED APPLICATION

This application claims priority under 35 U.S.C. §119(e) to U.S. Provisional Application No. 60/286,379, filed Apr. 26, 2001, which is incorporated herein by reference.

BACKGROUND OF THE INVENTION

1. Field of the Invention

The invention relates to novel strains of the fungus *Rhizopus oryzae* and uses thereof.

2. Background Art

Lactic acid and its salts can be used as components of food, pharmaceuticals, cosmetics, and agrichemicals. For example, lactic acid has been used in the production of confectionary products, beer, wine, dairy products, soft drinks, jams, salad dressings, and biodegradable polymers.

Lactic acid can be produced by synthetic or fermentative methods. In synthetic methods, lactonitrile is converted to lactic acid. In fermentative methods, bacteria or other microorganisms produce lactic acid as they metabolize carbon-containing materials. For example, homofermentative bacteria such as *Lactobacillus, Streptococcus,* or *Pediococcus* can metabolize a carbon source, e.g., a carbohydrate, to produce lactic acid.

BRIEF SUMMARY OF THE INVENTION

The invention provides novel, temperature-resistant strains of *Rhizopus oryzae,* and mutants thereof. These novel strains can be used to produce lactic acid at high temperatures.

Accordingly, the invention features the *Rhizopus oryzae* strains ADM 34:31 (Accession No. NRRL 30427), ADM 47.26 (Accession No. NRRL 30430), ADM 48.6 (Accession No. NRRL 30431), ADM 48.80 (Accession No. NRRL 30432), ADM 50.48 (Accession No. NRRL 30433), ADM 34.34 (Accession No. NRRL 30428), ADM 34.89 (Accession No. NRRL 30429), and ADM 33.30 (Accession No. NRRL 30426), as well as mutants thereof that convert a carbon source to lactic acid. Each of these *Rhizopus oryzae* strains were deposited under the Budapest Treaty on Mar. 9, 2001 in the Agricultural Research Culture Collection (NRRL), 1815 N. University Street, Peoria, Ill. U.S.A. and have been assigned the above-identified accession numbers. Preferably, the mutant converts dextrose to lactic acid at a rate of at least 0.5 grams/Liter/hour at 40° C. If desired, the strain may contain a genetically engineered vector.

The *Rhizopus oryzae* strains of the invention can be used in a method for producing lactic acid, the method comprising culturing the strain in a medium comprising a carbon source (e.g., a sugar or starch), and allowing the strain to metabolize the carbon source, thereby producing lactic acid. The lactic acid then can be isolated from the medium. Alternatively, the lactic acid can be converted to a lactate salt (e.g., calcium L-lactate, sodium L-lactate, potassium L-lactate, or ammonium L-lactate). The lactate salt subsequently can be isolated from the medium.

In various embodiments, the strain is cultured at 38° C. to 46° C., e.g., at 40° C. to 42° C. In other embodiments, the strain is cultured at a first temperature and subsequently cultured at a second temperature, wherein the second temperature is higher than the first temperature. For example, the first temperature may be 28° C. to 36° C. (e.g., 32° C. to 34° C.), and the second temperature may be 38° C. to 46° C. (e.g., 40° C. to 42° C.).

In another embodiment, the strain is cultured first under conditions that favor growth of *Rhizopus oryzae,* and the strain is subsequently cultured under conditions that inhibit growth of *Rhizopus oryzae.*

The invention also features a method for isolating colonies of *Rhizopus* sp., e.g., *Rhizopus oryzae.* Colonies of *Rhizopus* can be isolated by providing a suspension of a *Rhizopus* strain in a solution comprising a detergent (e.g., a nonionic surfactant such as Triton X-100) or other agent that will inhibit aggregation of spores, transferring the suspension to a first LPM agar plate, incubating the strain on the plate for a time sufficient to allow the growth of *Rhizopus* colonies on the plate (e.g., 3 to 4 days, e.g., at a high temperature such as 38–46° C. (e.g., 40° C.) to slow mycelial growth), transferring at least one of the colonies to a second LPM agar plate, incubating the colony on the plate (e.g., for 2 days, e.g., at 38–46° C. (e.g., 40° C.)), and isolating a sector of the second LPM agar plate comprising all or a portion of the colony. For example, the sector can be isolated by using a plastic transfer pipette to pluck a section of agar from the plate. LPM agar plates include $KH_2PO_4$ (about 0.6 g/L), $MgSO_4 \cdot 7H_2O$ (about 0.25 g/L), $Zn_2SO_4 \cdot 7H_2O$ (about 0.005 g/L), $(NH_4)_2HPO_4$ (about 1 g/L), dextrose (about 5 g/L, adjusted to pH 5.5), and agar (about 15 g/L).

If desired, the method can also include inoculating a potato-dextrose-agar (PDA) slant with the sector containing the *Rhizopus.* The PDA slant can be incubated for a time sufficient to allow the formation of *Rhizopus* spores. The method can also include isolating spores from the PDA slant and inoculating a medium with the isolated spores. If desired, the isolated spores may be suspended in a solution comprising a nonionic detergent (e.g., Triton X-100) prior to inoculating the medium.

If desired, the *Rhizopus* strain may be a strain of *Rhizopus oryzae,* such as, without limitation, ADM34.31 (NRRL 30427), ADM47.26 (NRRL 30430), ADM48.6 (NRRL 30431), ADM48.80 (NRRL 30432), ADM50.48 (NRRL 30433), ADM34.34 (NRRL 30428), ADM34.89 (NRRL 30429), and ADM33.30 (NRRL 30426), or mutants thereof. Colonies of other *Rhizopus* stains also can be isolated, for example, by providing a suspension of *Rhizopus* that includes a plurality of mutant *Rhizopus* stains.

The invention offers several advantages. The strains of the invention can be used at high temperatures for the production of lactic acid and/or its salts. By carrying out fermentation at a high temperature (e.g., 38° C. to 46° C.), the precipitation of lactate (e.g., calcium L-lactate), which can interfere with fermentation, is inhibited or prevented. Fermentation at high temperatures also provides higher titers of lactic acid production than does fermentation at conventional temperatures. Other features and advantages of the invention will be apparent from the following detailed description of the invention, and from the claims.

DETAILED DESCRIPTION OF THE INVENTION

The invention provides novel strains of *Rhizopus oryzae,* which can be used, inter alia, in the production of lactic acid. Included within the invention are the novel strains: ADM34.31 (NRRL 30427), ADM47.26 (NRRL 30430), ADM48.6 (NRRL 30431), ADM48.80 (NRRL 30432), ADM50.48 (NRRL 30433), ADM34.34 (NRRL 30428), ADM34.89 (NRRL 30429), and ADM33.30 (NRRL 30426), as well as mutants thereof that convert a carbon source to lactic acid.

The strains of the invention are temperature-resistant strains of *Rhizopus oryzae*. Such strains are capable of converting a carbon lactic acid when cultured at 40° C.

Mutant strains of the invention can be produced using conventional methods to mutagenize strain(s) ADM34.31 (NRRL 30427), ADM47.26 (NRRL 30430), ADM48.6 (NRRL 30431), ADM48.80 (NRRL 30432), ADM50.48 (NRRL 30433), ADM34.34 (NRRL 30428), ADM34.89 (NRRL 30429), and ADM33.30 (NRRL 30426). For example, mutagenesis can be carried out using N-methyl-N'-nitro-N-nitrosoguanidine (NTG), as described herein. Preferably, the mutant strains convert dextrose to lactic acid at 40° C.

Conventional media for growing *Rhizopus oryzae* can be used in the methods of the invention. For example, to germinate mycelia, suspensions of *Rhizopus* spores can be cultured in a medium such as a seed medium (e.g., $KH_2PO_4$ 0.6 g/L, $MgSO_4.7H_2O$ 0.25 g/L, $Zn_2SO_4.7H_2O$ 0.088 g/L, $CaCO_3$ 15 g/L, starch 25 g/L, dextrose 100 g/L, urea 2 g/L (filter sterilized separately), pH adjusted to 5.8). After the mycelia are germinated (typically in 16 to 30 hours), the mycelial seed can be transferred to a fermentation medium (e.g., $MgSO_4.7H_2O$ 5 g/L, $Fe_2(SO_4)_3$ 0.001 g/L, $MnSO_4.H_2O$ 0.02 g/L, $KH_2PO_4$ 0.6 g/L, $CaCO_3$ 67 g/L, dextrose 110 g/L, corn oil 1 mL/L, urea 1 g/L (filter sterilized separately), pH adjusted at 7.4). Other media in which *Rhizopus oryzae* can grow can be used in the invention. For example, as an alternative to the use of dextrose, the medium may use an alternate carbon source.

A variety of carbon-containing materials can be included in the medium as the carbon source that is metabolized by *Rhizopus oryzae* into lactic acid. For example, sugars such as dextrose, glucose, or sucrose can be used. Also, carbon-containing raw materials such as barley, cassava, corn, oats, wheat, sorghum, molasses, cheese whey, milo, potato, rye, sweet potato, Jerusalem artichoke, rice or the like can be used. Other useful carbon sources include, without limitation, potato waste materials, grape juice, grape pomace, apple pomace, and raisins.

During culturing of *Rhizopus oryzae*, the pH of the medium preferably is controlled such that it remains between pH 4 and pH 6. The pH can be lowered by adding to the medium a basic substance, such as calcium carbonate, sodium carbonate, ammonium carbonate, potassium carbonate, sodium hydroxide, potassium hydroxide, or ammonium hydroxide, which will neutralize the lactic acid and produce a lactate salt.

If desired, culturing of *Rhizopus* can be carried out in two or more stages. For example, the first stage of culturing may be carried out at about 28° C. to 36° C. (e.g., at 29, 30, 31, 32, 33, 34, or 35° C.). Typically, this stage of culturing is carried out for about 10 to 24 hours (e.g., about 12 to 18 hours). Subsequently, the temperature of the culture is raised to about 38° C. to 46° C. (e.g., 39, 40, 41, 42, 43, 44 or 45° C.), and culturing is continued. Typically, the second stage of culturing also is carried out for about 10 to 60 hours (e.g., about 12 to 50 hours). Once the carbon source is metabolized into lactic acid, culturing typically is discontinued.

In an alternative two-stage method, the first stage utilizes culture conditions that are favorable for growth, and the second stage utilizes culture conditions that are favorable for lactic acid production and which conditions inhibit growth of the strain, e.g., as described in U.S. Pat. No. 5,786,185.

In this method, the pH of the medium during the first stage is preferably kept near the optimum growth pH for *Rhizopus oryzae*, e.g., pH 4 to pH 6. An exemplary medium that is favorable for cell growth includes: glucose 80 g/L, yeast extract 48 g/L, $MgSO_4.7H_2O$ 1.34 g/L, $FeSO_4.7H_2O$ 0.06 g/L, $MnSO_4.7H_2O$ 0.042 g/L, sodium acetate 1.23 g/L, and $K_2PO_4$ 0.062 g/L. Once the desired cell density has been reached, the fermentative production of lactic acid is conducted under conditions that inhibit growth of *Rhizopus*, e.g., by fermentation in a medium that lacks a nitrogen source. An exemplary medium includes 100 g/L, $MgSO_4.7H_2O$ 0.25 g/L, $KH_2PO_4$ 0.60 g/L, and $FeCl_4$ 0.05 g/L. Fermentation under conditions that inhibit fungal growth are favorable for lactic acid production because the available carbon source can be used for lactic acid production rather than for cell growth. Optionally, the growth-inhibiting medium can be temporarily replaced, periodically, with a growth-supporting medium.

Optionally, fermentation can be carried out using *Rhizopus* strains of the invention that are immobilized on a solid support. For example, the solid support for immobilization of the *Rhizopus* strains can be made of a synthetic polymer such as a polyolefin, in admixture with an organic polymeric plant material such as corn fibers, oat hulls, starch, and/or cellulose, e.g., as described in U.S. Pat. No. 5,595,893. Preferably, the synthetic polymer is present in an amount of about 50–95 wt % and the plant material is present in an amount of about 5–50 wt %. Examples of suitable polyolefins include polyethylene and polypropylene. The plant material may be a mixture that includes a plant material which functions as a nutrient to enhance growth of the *Rhizopus* strain on the support. The support may be produced by combining the synthetic polymer and plant material to form a composite, dough-like thermoplastic composition (See, e.g., U.S. Pat. No. 5,595,893). By immobilizing the *Rhizopus* strain on a solid support, fermentation can be carried out in a continuous process. Alternatively, batch fermentation processes can be used.

Lactic acid produced by the strains of the invention can be converted to a salt form thereof, i.e., L-lactate, or the free lactic acid can be isolated from the fermentation medium. To produce L-lactate, lactic acid is neutralized with a basic substance such as sodium hydroxide, ammonium hydroxide, sodium carbonate, calcium carbonate, or ammonium carbonate. Typically, the basic substance is included in the fermentation medium in an amount sufficient to neutralize the lactic acid produced during fermentation.

Conventional methods can be used to isolate the lactate salt. For example, calcium L-lactate can be precipitated from solution by lowering the temperature of the solution to about 4° C., e.g., as described in U.S. Pat. No. 4,963,486.

If desired, the isolated lactate salt then can be converted into lactic acid using conventional techniques. For example, a lactate salt solution can be applied to a cation exchange column to produce lactic acid, e.g., as described in U.S. Pat. No. 5,932,455. Alternatively, conventional electrodialysis methods can be used.

As an alternative, or in addition, to producing a lactate salt, free lactic acid can be isolated from the medium using conventional techniques. For example, free lactic acid can be isolated by contacting a lactic acid-rich medium with a solid-phase polymer that contains tertiary amine groups to adsorb the free lactic acid, e.g., as described, in U.S. Pat. No. 5,786,185. The tertiary amine functions of the adsorbent polymer can be provided by N-heterocyclic or by N-aliphatic groups, e.g., in their free base form. For example, AMBERLYST™ A-21 resin (Rohm and Haas; Philadelphia, Pa.) contains aliphatic tertiary amine functions and can be used to isolate free lactic acid. In other suitable polymers, the tertiary amine functions are pyridine functions, e.g., polyvinylpyridine polymers. For example, crosslinked polymers, such as REILLEX™ polymers, can be used.

Typically, the fermentation medium is filtered to remove the *Rhizopus* prior to contacting the polymer with the fermentation medium. The filtered fermentation medium containing lactic acid then is passed through a column containing the desired polymer, and the free lactic acid is bound to the column. After the polymer is saturated, the polymer preferably is washed with water, and the adsorbed lactic acid then is recovered using a desorbing agent. Examples of suitable desorbing agents include polar organic solvents (e.g., an alcohol such as methanol) or hot water. After the lactic acid is eluted from the column, the lactic acid can be treated in a conventional matter, e.g., concentrated by evaporation or distillation.

If desired, a *Rhizopus* strain of the invention can be transformed with a genetically engineered vector to express a coding sequence in the strain. Conventional methods and vectors can be used. For example, the vector can be engineered such that it will become integrated into the genome of the *Rhizopus* strain. An exemplary method for transforming *Rhizopus* with a multicopy integration vector is described in U.S. Pat. No. 6,004,776.

EXAMPLE 1

Isolation of High Temperature-Resistant Mutants of *Rhizopus oryzae*

The *Rhizopus oryzae* strains of the invention, which are high temperature-resistant and which produce L-lactic acid, were isolated as follows. A non-temperature-resistant *Rhizopus oryzae* strain developed from *Rhizopus oryzae* NRRL 395 was cultivated on PDA slants (Difco) at 30° C. for about 7 days to produce spores. Approximately 6 mL of 0.1% Triton X-100 (Sigma) solution was then added to each slant to wash off spores from mycelia on the agar surface. The spores were suspended in 3 mL TM-Triton buffer (Tris.HCl 6.0 g/L, maleic acid 5.8 g/L, $(NH_4)_2SO_4$ 1.0 g/L, $Ca(NO_3)_2$ 5 mg/L, $MgSO_4.7H_2O$ 0.1 g/L, $FeSO_4.7H_2O$ 0.25 mg/L, Triton X-100 0.1%, adjusted to pH 6.0 using KOH).

For mutagenesis, N-methyl-N'-nitro-N-nitrosoguanidine (NTG) was added to the spore suspension at a concentration of 100 mg/L, and the spores were treated with NTG at room temperature for 30 minutes. After 30 minutes, 10 mL TM-Triton buffer was then added to the NTG-treated spore suspension. The treated spores were pelleted by centrifugation and washed twice with buffer. The collected NTG-treated spores were then resuspended in 0.1% Triton X-100 and spread onto LPM agar plates ($KH_2PO_4$ 0.6 g/L, $MgSO_4.7H_2O$ 0.25 g/L, $Zn_2SO_4.7H_2O$ 0.005 g/L, $(NH_4)_2HPO_4$ 1 g/L, dextrose 5 g/L, adjusted to pH 5.5, agar 15 g/L) and incubated at 40° C. for 3–4 days.

Colonies growing on 40° C. LPM plates were isolated and transferred to another LPM plate. After two more days of incubation at 40° C., colonies were then transferred to a PDA slant. The slant cultures of isolated mutants were incubated at 30° C. for 7 days to produce spores. A spore suspension prepared in 0.1% Triton X-100 solution as described above was used to inoculate a shaker flask of medium for assays of L-lactic acid production.

In the same experiment, NTG-treated and untreated (control) spore suspensions also were spread on LPM agar plates and incubated at 30° C. for one day. Colonies that developed on these plates were counted. As estimated by the number of non-mutagenized, control spores, NTG treatment killed 97.8% of the spores in the mutagenized spore suspension.

EXAMPLE 2

Temperature-Shifted Fermentation in Shaker Flasks Using High Temperature-Resistant *Rhizopus oryzae*

In this example, a two-stage fermentation method is disclosed in which the strain is cultured at a first temperature (34° C.) and then subsequently cultured at a second, higher, temperature (40° C.). In this example, strains were selected for temperature-shifted fermentation by screening temperature-resistant mutants of *Rhizopus oryzae* grown by shaker flask fermentation at two different temperatures.

Approximately $1-5\times10^6$ spores in 0.1–0.2 mL of spore suspension solution, prepared as described in Example 1, were used to inoculate 50 mL of shaker flask seed medium [$KH_2PO_4$ 0.6 g/L, $MgSO_4.7H_2O$ 0.25 g/L, $Zn_2SO_4.7H_2O$ 0.088 g/L, $CaCO_3$ 15 g/L, starch 25 g/L, dextrose 100 g/L, urea 2 g/L (filter sterilized separately), pH adjusted to 5.8] in a 250 mL baffled shaker flask. To germinate mycelia, the culture was then incubated for 20 hours at 34° C. with shaking at 120 rpm.

After 20 hours, 2 mL mycelial seed were transferred to another 250 mL shaker flask containing 20 mL of shaker flask fermentation medium [$MgSO_4.7H_2O$ 5 g/L, $Fe_2(SO_4)_3$ 0.001 g/L, Mn $SO_4.H_2O$ 0.02 g/L, $KH_2PO_4$ 0.6 g/L, $CaCO_3$ 67 g/L, dextrose 110 g/L, corn oil 1 mL/L, urea 1 g/L (filter sterilized separately), pH adjusted at 7.4]. The shaker flask fermentation was carried out at 34° C. for the first 14 hours, with shaking at 120 rpm. After 14 hours, the temperature was shifted to 40° C., and the culture was maintained at 40° C. for 14 additional hours.

After a total of 28 hours of fermentation, the production of L-lactic acid from a selected strain, ADM34.31, and its parent *Rhizopus oryzae* strain was measured by HPLC using conventional methods (Simadzu LC10AT pump, Simadzu RID-10A refractive index detector, and Bio-Rad Aminex HPX-87H column). As shown in Table 1, strain ADM34.31 produced increased levels of L-lactic acid, relative to the parental strain.

TABLE 1

| Strain | L-lactic acid (g/L) | Yield (%) |
| --- | --- | --- |
| Parental *Rhizopus oryzae* strain | 34.3 | 87.5 |
| ADM34.31 | 77.8 | 92.6 |

EXAMPLE 3

Temperature-Shifted Fermentation in Shaker Flasks Using High Temperature-Resistant *Rhizopus oryzae*

In this example, a two-stage fermentation method was employed as in Example 2 to isolate additional temperature-resistant stains of *Rhizopus oryzae*. However, in this example, cultures in shaker flasks were first grown at 34° C. with shaking at 120 rpm for 12 hours and then the temperature was shifted to 42° C. and maintained at 42° C. for an additional 12 hours. Samples were then analyzed by HPLC for lactic acid production as described in Example 2. Table 2 provides a list of the temperature-resistant strains, their titers (g/L), and the yield of lactic acid obtained with each strain. As compared with the parental *Rhizopus oryzae* strain described in Example 2, increased lactic acid production (g/L) was achieved with the novel strains ADM47.26, ADM48.6, ADM48.80, and ADM50.48.

TABLE 2

| Strain   | L-lactic acid (g/L) | Yield (%) |
|----------|---------------------|-----------|
| ADM47.26 | 57.9                | 83.4      |
| ADM48.6  | 63.2                | 95.2      |
| ADM48.80 | 76.2                | 96.5      |
| ADM50.48 | 80.7                | 97.5      |

EXAMPLE 4

Temperature-Shifted Fermentation in an Air-Lifted Fermentor

This example illustrates that the *Rhizopus oryzae* strains of the invention can be used in air-lift fermentors in scaled-up, temperature-shifted fermentation methods.

Fermentors containing seed media composed of 100 g/L dextrose, 16 g/L (dry basis) corn steep liquor, 0.6 g/L $KH_2PO_4$ and 0.03 mL/L antifoam were inoculated separately with 1000 spores/mL of spore suspensions of strains ADM34.31, ADM34.34, ADM34.89 and ADM33.30. The cultures were grown in 7.5 L air-lift fermentors at 34° C. and 1.5 vvm air. The initial pH of the media was left as is, and the pH control point during incubation was 4.8. $NH_4OH$ was used for pH control.

Sufficient cell mass, as determined by packed cell volume, was present after 16.5 hours of incubation, and a portion of the broths, amounting to 6% of the production media volume, was transferred to the production fermentor. Production media consisted of 100 g/L dextrose, 0.55 g/L $Ca(H_2PO_4)_2 \cdot H_2O$, 0.1 g/L urea, 0.03 mL/L antifoam and 49 g/L $CaCO_3$.

The urea and $CaCO_3$, prepared as a 22% w/v slurry, were sterilized separately. The urea and 3 g/L of $CaCO_3$ were added just prior to inoculation; the remaining $CaCO_3$ was added when the fermentation pH dropped below 4.5. The fermentations were conducted in 7.5 L vessels with 1.5 vvm air flow and the initial pH was left as is. In this two-stage fermentation process, the initial temperature was 34° C. After 12 hours of cultivation, the temperature was shifted to 40° C.

The fermentations were complete in 54 to 61.5 hours, at which point all of the dextrose had been consumed. The final titers (g/L), production rates (g/L/hr) and yields of calcium L-lactate are listed in Table 3. The production rates were calculated as: the total grams of lactic acid produced divided by the starting volume of the culture divided by the number of hours of fermentation. No precipitation of calcium L-lactate was observed in any of the cultures. As compared with the parental *Rhizopus oryzae* strain, the strains of the invention produce lactic acid at an increased titer and rate.

TABLE 3

| Strain   | Lactic (g/L) | Rate (g/L/hr) | % Yield |
|----------|--------------|---------------|---------|
| ADM33.30 | 80.7         | 1.086         | 74.1    |
| ADM34.31 | 88.9         | 1.429         | 86.2    |

TABLE 3-continued

| Strain   | Lactic (g/L) | Rate (g/L/hr) | % Yield |
|----------|--------------|---------------|---------|
| ADM34.34 | 84.8         | 1.384         | 82.8    |
| ADM34.89 | 90.1         | 1.199         | 80.8    |

EXAMPLE 5

Temperature-Shifted Fermentation at Various Concentrations of Dextrose

Using strain ADM 34.31, fermentations were carried out in the media described in Example 4 but with dextrose concentrations of 110 g/L or 120 g/L in the lactic acid production stage. The same operating parameters were employed, with the temperature being raised from 34° C. to 40° C. after 12 hours of fermentation time in the production stage. The results obtained with fermentation under these conditions are provided in Table 4.

TABLE 4

| Dextrose conc. | Age (hours) | Lactic (g/L) | Rate (g/L/hr) | % Yield |
|----------------|-------------|--------------|---------------|---------|
| 110 g/L        | 72.25       | 110          | 1.190         | 90.2    |
| 120 g/L        | 72.25       | 109          | 1.275         | 88.9    |

In summary, the examples disclosed herein illustrate that the claimed strains can be used to produce lactic acid at high titers and rates and with high yields.

The foregoing examples are illustrative only and are not intended to limit the scope of the invention as defined by the appended claims. It will be apparent to those skilled in the art that various modifications and variations can be made in invention without departing from the spirit and scope of the invention. Thus, it is intended that the present invention cover the modifications and variations of this invention provided they come within the scope of the appended claims and their equivalents.

All patents and publications referred to herein are expressly incorporated herein by reference.

What is claimed is:

1. An isolated *Rhizopus oryzae* strain selected from the group consisting of ADM 34.31 (NRRL 30427), ADM 47.26 (NRRL 30430), ADM 48.6 (NRRL 30431), ADM 48.80 (NRRL 30432), ADM 50.48 (NRRL 30433), ADM 34.34 (NRRL 30428), ADM 34.89 (NRRL 30429), and ADM 33.30 (NRRL 30426), and mutants thereof that convert a carbon source to lactic acid.

2. The strain of claim 1, wherein the strain is a mutant of a strain selected from the group consisting of *Rhizopus oryzae* ADM 34.31 (NRRL 30427), ADM 47.26 (NRRL 30430), ADM 48.6 (NRRL 30431), ADM 48.80 (NRRL 30432), ADM 50.48 (NRRL 30433), ADM 34.34 (NRRL 30428), ADM 34.89 (NRRL 30429), and ADM33.30 (NRRL30426) that converts dextrose to lactic acid at a rate of at least 0.5 grams/Liter/hour at 40° C.

3. A method for producing lactic acid, the method comprising culturing the strain of claim 1 in a medium comprising a carbon source and allowing said strain to metabolize said carbon source, thereby producing lactic acid.

4. The method of claim 3, further comprising isolating said lactic acid from said medium.

5. The method of claim 3, further comprising converting said lactic acid to a salt thereof.

6. The method of claim 5, wherein said lactic acid is converted to a salt selected from the group consisting of calcium L-lactate, sodium L-lactate, potassium L-lactate, and ammonium L-lactate.

7. The method of claim 3, wherein said strain is cultured at a temperature of 38° C. to 46° C.

8. The method of claim 7, wherein said strain is cultured at a temperature of 40° C. to 42° C.

9. The method of claim 3, wherein said strain is cultured at a first temperature and subsequently cultured at a second temperature, wherein said second temperature is higher than said first temperature.

10. The method of claim 9, wherein said first temperature is 28° C. to 36° C.

11. The method of claim 10, wherein said first temperature is 32° C. to 34° C.

12. The method of claim 9, wherein said second temperature is 38° C. to 46° C.

13. The method of claim 12, wherein said second temperature is 40° C. to 42° C.

14. The method of claim 3, wherein said strain is cultured first under conditions that favor growth of *Rhizopus oryzae*, and said strain is subsequently cultured under conditions that inhibit growth of *Rhizopus oryzae*.

15. An isolated *Rhizapus oryzae* strain consisting of one of ADM 34.31 (NRRL 30427) and a mutant thereof that converts a carbon source to lactic acid.

16. The isolated *Rhizopus oryzae* strain of claim 15, consisting of ADM 34.31 (NRRL 30427).

17. An isolated *Rhizopus oryzae* strain consisting of one of ADM 47.26 (NRRL 30430) and a mutant thereof that converts a carbon source to lactic acid.

18. The isolated *Rhizopus oryzae* strain of claim 17, consisting of ADM 47.26 (NRRL 30430).

19. An isolated *Rhizopus oryzae* strain consisting of one of ADM 48.6 (NRRL 30431) and a mutant thereof that converts a carbon source to lactic acid.

20. The isolated *Rhizopus oryzae* strain of claim 19, consisting of ADM 48.6 (NRRL 30431).

21. An isolated *Rhizopus oryzae* strain consisting of one of ADM 48.80 (NRRL 30432) and a mutant thereof that converts a carbon source to lactic acid.

22. The isolated *Rhizopus oryzae* strain of claim 21, consisting of ADM 48.80 (NRRL 30432).

23. An isolated *Rhizopus oryzae* strain consisting of one of ADM 50.48 (NRRL 30433) and a mutant thereof that converts a carbon source to lactic acid.

24. The isolated *Rhizopus oryzae* strain of claim 23, consisting of ADM 50.48 (NRRL 30433).

25. An isolated *Rhizopus oryzae* strain consisting of one of ADM 34.34 (NRRL 30428) and a mutant thereof that converts a carbon source to lactic acid.

26. The isolated *Rhizopus oryzae* strain of claim 25, consisting of ADM 34.34 (NRRL 30428).

27. An isolated *Rhizopus oryzae* strain consisting of one of ADM 34.89 (NRRL 30429) and a mutant thereof that converts a carbon source to lactic acid.

28. The isolated *Rhizopus oryzae* strain of consisting of claim 27, ADM 34.89 (NRRL 30429).

29. An isolated *Rhizopus oryzae* strain consisting of ADM 33.30 (NRRL 30426) and a mutant thereof that converts a carbon source to lactic acid.

30. The isolated *Rhizopus oryzae* strain of claim 29, consisting of ADM 33.30 (NRRL 30426).

* * * * *

UNITED STATES PATENT AND TRADEMARK OFFICE
CERTIFICATE OF CORRECTION

PATENT NO. : 6,849,444 B2  Page 1 of 1
APPLICATION NO. : 10/127679
DATED : February 1, 2005
INVENTOR(S) : Hungming Liaw It is certified that error appears in the above-identified patent and that said Letters Patent is hereby corrected as shown below:

OTHER PUBLICATIONS: Column 2, insert comma after "acid."

CLAIMS: Claim 28, insert --claim 27-- after "strain of" therefor.

Column 2, Lines 45 and 47, delete "stains" and insert --strains-- therefor.

Column 3, Line 6, delete "carbon lactic acid" and insert --carbon source (e.g., dextrose) to lactic acid-- therefor.

Column 6, Line 61, delete "stains" and insert --strains-- therefor.

Column 8, Line 34, insert --the-- after "in" therefor.

Signed and Sealed this

Twenty-second Day of January, 2008

JON W. DUDAS
*Director of the United States Patent and Trademark Office*